United States Patent [19]
Barr et al.

[11] 3,953,844
[45] Apr. 27, 1976

[54] INCIPIENT FIRE DETECTOR

[75] Inventors: Laurence Gibson Barr, Mission Viejo; Raymond Lu-po Chuan, Altadena; James Fredrick Harkee, Glendora, all of Calif.

[73] Assignee: Celesco Industries Inc., Costa Mesa, Calif.

[22] Filed: Apr. 11, 1973

[21] Appl. No.: 350,091

[52] U.S. Cl. ............................ 340/237 S; 73/28; 73/421.5 A; 340/236
[51] Int. Cl.² ...................................... G08B 17/10
[58] Field of Search ............ 340/237 S, 236; 73/28, 73/421.5 A; 324/71 CP

[56] References Cited
UNITED STATES PATENTS

| | | | |
|---|---|---|---|
| 3,289,481 | 12/1966 | Barnes | 73/421.5 A |
| 3,653,253 | 4/1972 | Olin | 73/28 |
| 3,715,911 | 2/1973 | Chuan | 73/28 |

FOREIGN PATENTS OR APPLICATIONS

| | | | |
|---|---|---|---|
| 796,010 | 6/1958 | United Kingdom | 73/421.5 A |

*Primary Examiner*—John W. Caldwell
*Assistant Examiner*—Daniel Myer
*Attorney, Agent, or Firm*—Finnegan, Henderson, Farabow & Garrett

[57] ABSTRACT

The incipient fire detector employs a particulate monitor for detecting particulates in the atmosphere. During an incipient fire condition, prior to ignition, a large mass of particulates less than .5 microns in size is generated by the combustible material which increases the concentration of such particulates in the atmosphere. The detector samples and responds to the rate of increase of such particulates to provide an alarm when such rate exceeds a predetermined rate indicative of a hazardous condition. The particle collector employed in the incipient fire detector is specially designed to collect particulates less than five microns in size and reject those above this size.

24 Claims, 6 Drawing Figures

INCIPIENT FIRE DETECTOR

BACKGROUND OF THE INVENTION

The present invention is directed to fire detection apparatus and more particularly to an incipient fire detector employing a particulate monitor.

There are many fire detection systems and devices available, and their operation is based on a wide variety of principles. Most require the presence of flame, fly ash ("smoke"), attainment of a preset temperature level, or the like, and thus that the fire actually exists before it can be detected. It is understood that many of these are complex, subject to contamination, false alarm prone, and/or fail to detect fires under use conditions.

It was felt that a need existed for fire-detection apparatus which could detect a fire in its incipiency, that is, could detect and warn of a hazardous condition that if unattended might lead to a fire, and do this detection with a significant reduction in, and the possibility of complete elimination of, false alarms. This type of detector would have general utility, but would be particularly advantageous for use in isolated areas, aircraft, space vehicles, submarines, and where large concentrations of electronic equipment are present as in computer facilities, to name a few examples. To meet this need, the present invention was devised.

A study was undertaken to find an inherent by-product of an incipient fire condition that could be reliably detected without false alarms. It was found that when combustible materials are heated, some parts may vaporize and recondense in the air as sub-micron particulates thus increasing significantly the concentration of small particulates beyond the distribution normally present. It was subsequently learned that this phenomena of a large flux of sub-micron particles being present during an incipient fire condition had previously been observed by others.

This abnormal increase in sub-micron particulates invariably precedes the onset of combustion. Tests were run during the study on a variety of materials to verify this phenomena. For example, there is a wide variation in the ignition temperature of Coolanol 35 and silicone rubber. In tests of both substances using a gradual increase in temperature, the signals obtained were similar even though the temperatures at which the signals occurred were widely different. As the temperature rose in both cases toward the ignition point, the signal remained steady until pre-pyrolitic decomposition occurred just before ignition. At this time an abnormal sub-micron-particle emission took place and was detected.

SUMMARY OF THE INVENTION

The abnormal increase in sub-micron particulate emission could only result from an abnormal energy increase. The detector of the present invention senses the occurrence of this increased emission and processes the signal to indicate that an abnormal energy increase is present at the location of the active sensor and that it requires immediate attention to avert a hazardous condition.

To achieve the objects of and in accordance with the purposes of the invention, as embodied and broadly described herein, the incipient fire detector of this invention comprises a collector for selectively collecting particulates from a fluid flowing past said collector, said collector having an outer surface, said outer surface being closed at the portion facing the direction of planned flow of said fluid, and an opening formed in the outer surface portion facing opposite to the direction of planned flow, said collector being sized to collect into said opening particulates having a size less than 5 microns and reject substantially all particulates having a size above 5 microns; means for sensing the particulates collected by said collector; means for directing said collected particulates from said collector opening to said sensing means; and means responsive to the output of said sensing means for processing an increase in the mass of particulates sensed by said sensing means as an indication of an incipient fire condition.

The incipient fire detector of this invention includes as part of the aforesaid processing means, means for detecting a rate of change in the output of said sensing means above a predetermined rate in response to an increase in the rate the mass of particulates is sensed by the sensing means; means for determining whether said predetermined rate is exceeded for a preset time duration; and means responsive to said determining means for indicating an incipient fire condition.

Further in accordance with the purposes of the invention, a collector is provided which selectively collects particulates from a fluid flowing past said collector, and comprises an outer surface, said outer surface being closed at the portion facing the direction of planned flow of the fluid; an opening formed in the outer surface portion facing opposite to the direction of planned flow; said collector being sized to collect into said opening particulates having less than a predetermined size and reject substantially all particulates above said predetermined size.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

The invention consists in the novel parts, constructions, arrangements, combinations, and improvements shown and described. The accompanying drawings, which are incorporated in and constitute a part of this specification, illustrate one embodiment of the invention and, together with the description, serve to explain the principles of the invention.

DESCRIPTION OF THE PREFERRED EMBODIMENT

Reference will now be made in detail to the present preferred embodiment of the invention, an example of which is illustrated in the accompanying drawings.

Figures 1, 5:
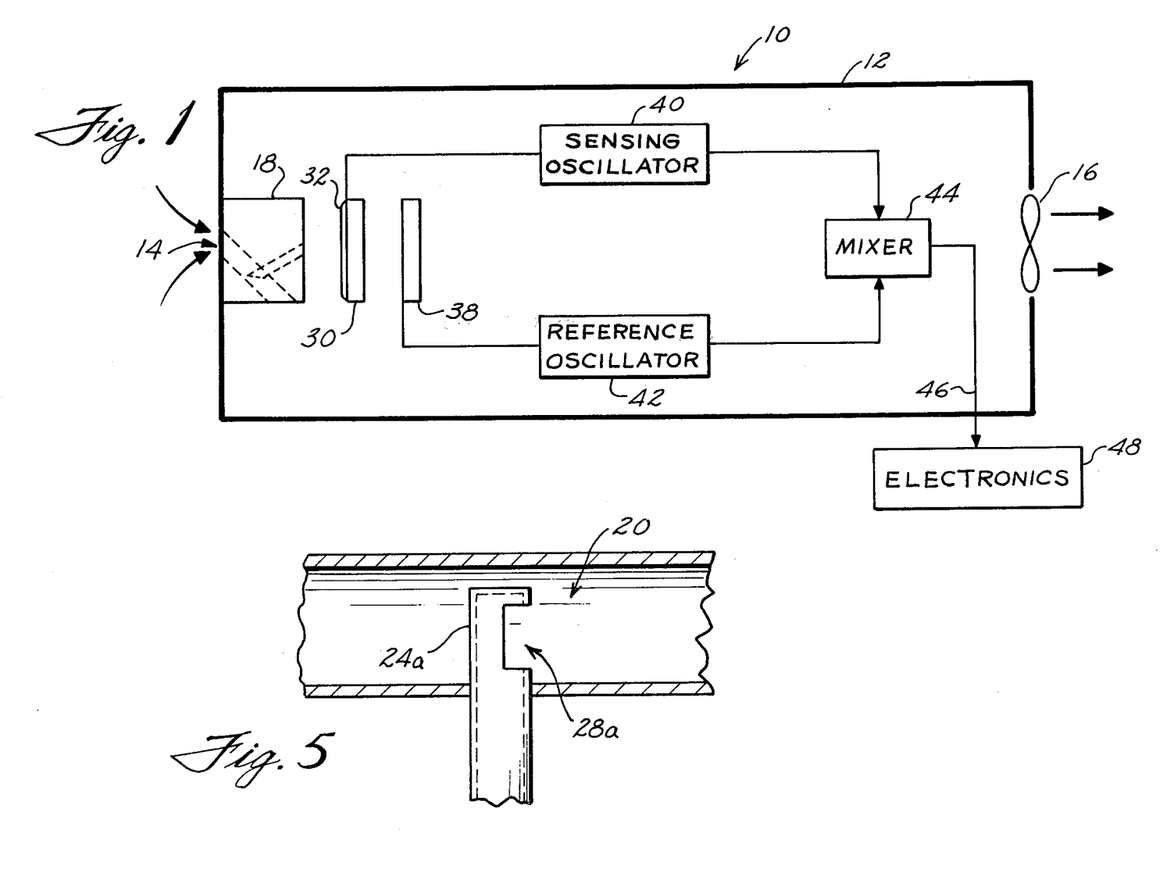
FIG. 1 is a schematic view of an improved incipient fire detector constructed in accordance with the teachings of this invention.
FIG. 5 is a side elevation view, partially in section, of an alternative embodiment of the collector tube used in the nozzle block.

Referring now to FIG. 1, there is presented a schematic view of an improved incipient fire detector indicated generally by the numeral 10. The detector 10 includes a housing 12 having an inlet 14, and a blower or fan 16 for drawing a particulate-laden sample of fluid, such as air, from the surrounding atmosphere into the inlet 14. Positioned at inlet 14 is a nozzle block or housing 18 through which the fluid sample passes.

Figure 2:
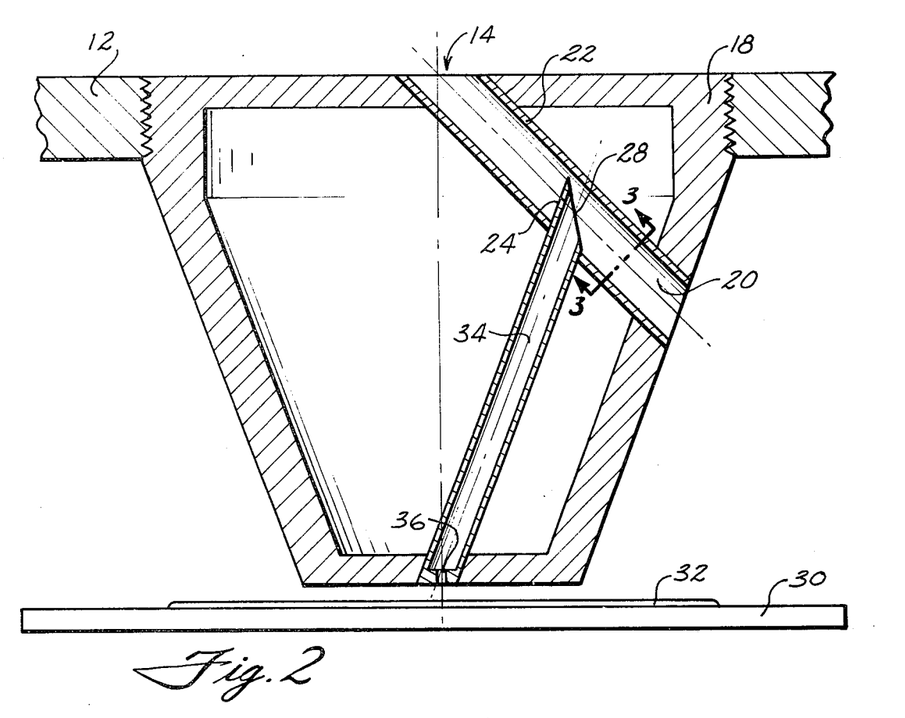
FIG. 2 is a side elevation view, in cross-section, of a preferred inlet nozzle block or housing used in the aforesaid incipient fire detector.

With additional reference to FIG. 2, there is shown in elevation a cross-sectional view of a preferred embodiment of a nozzle block 18. Block 18 can be made hollow, as shown here, or solid, if desired, and is preferably formed of a rigid light-weight material, such as aluminum or other suitable material, and is retained in housing 12 by threading or any other convenient means. As embodied herein, a passageway 20 is formed through the nozzle block or housing 18, and is in fluid-flow communication with the inlet 14 for passing a fluid sample through the nozzle block. Passageway 20 can be formed as the interior of a tube 22 inserted through nozzle block 18. Alternatively, where block 18 is made solid, passageway 20 can be conveniently formed by drilling an appropriately-sized hole through this block.

In accordance with the invention, a collector 24 is provided for selectively collecting particulates from a fluid flowing past said collector. This collector 24 is provided with an outer surface that is closed at the portion which faces the direction of planned flow of the fluid past the collector. The opening for collecting particulates from the fluid is formed in the outer surface portion of the collector which faces opposite to the direction of planned flow.

Figure 3:
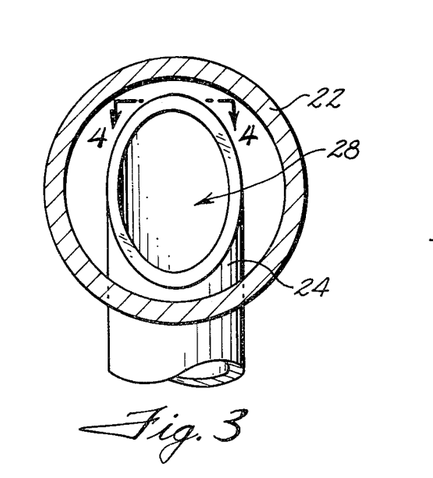
FIG. 3 is a sectional view taken along line 3—3 of FIG. 2 looking upstream through the main passageway of the nozzle block.
Figure 4:
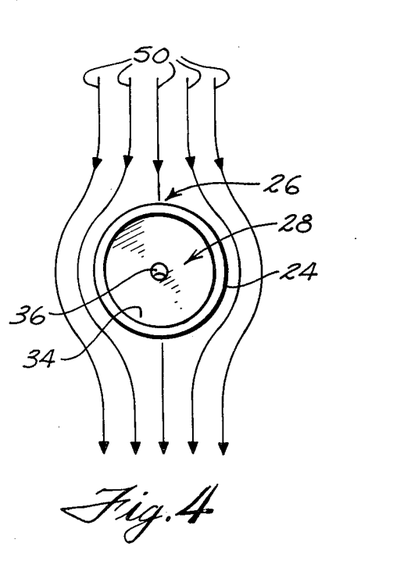
FIG. 4 is a plan view taken along line 4—4 of FIG. 3 looking down the longitudinal axis of the collector tube.

As here embodied, and with further reference to FIGS. 3 and 4, it is seen that the front surface 26 of collector 24 which faces upstream is closed. Preferably, this surface is formed as a curved surface to aid in deflecting the flow of fluid and particulates past the collector, as explained in greater detail hereinafter. As embodied herein, collector 24 is formed as a tube which extends into passageway 20, and has an opening 28 which is formed by cutting the tube at an oblique angle to its longitudinal access. This opening is preferably of a general elliptical shape when the collector tube 24 is viewed in elevation in FIG. 3. As shown, opening 28 faces in the downstream direction with reference to the planned flow of fluid through passageway 20.

In accordance with the invention, there are means provided for sensing the particulates collected by said collector. As embodied herein, this sensing means includes a sensing crystal 30 having a front surface on which the particulates captured by collector 24 are impacted. Preferably, a coating such as tacky coating 32 is applied to the front surface of crystal 30 to aid in retaining the particulates once they have impacted against this surface. Crystal 30 is designed to oscillate in a shear mode in which the opposite faces of the crystal execute parallel displacements. In this oscillation mode, the frequency of oscillation is affected by the mass on the crystal surface.

In accordance with the invention, means are provided for directing the collected particulates from the opening 28 of the collector to the sensing means. As embodied herein, said directing means includes the passageway 34 of collector tube 24 which is in flow communication with tube opening 28. The lower end of tube 24 terminates at the bottom of nozzle block 18, the latter being positioned closely adjacent to the surface of crystal 30. For example, a spacing of 0.004 inch has been found suitable to help insure that virtually all of the particulates captured by collector 24 will impact upon the surface of crystal 30. To aid in this impaction, the directing means further includes a nozzle 36 formed as a constricted opening in passageway 34 at the lower end of tube 24. This nozzle is designed to accelerate the collected fluid and particulates as they leave passageway 34 to help insure that the particulates are directed against the surface of the closely-spaced crystal 30. In this manner the sensitivity of crystal response is optimized.

In accordance with the invention, means are provided responsive to the output of the sensing means for processing an increase in the mass of particulates as an indication of an incipient fire condition. As embodied herein, this processing means comprises a reference crystal 38 spaced from sensing crystal 30. Reference crystal 38 is preferably matched to the sensing crystal 30 and is located within housing 12. In the embodiment shown, the processing means also comprises a means for oscillating the sensing crystal at its resonant frequency and a means for oscillating the reference crystal at a predetermined frequency. Preferably, these means include sensing oscillator 40 which is connected to sensing crystal 30, and a reference oscillator 42 which is connected to reference crystal 38. The latter crystal can be caused to vibrate either at the same frequency as sensing crystal 30 or at a second frequency having a predetermined difference from the resonant frequency of sensing crystal 30. Crystal oscillators 40 and 42 are well known in the art and suitable circuits can readily be found in the published literature. Oscillator 40 is preferably designed to have stability over the wide range of frequency shifts which are to be expected in view of the planned deposition of particulates on the crystal surface. In addition, oscillator 40 preferably shows stability over a wide range of temperature, humidity, and other environmental conditions encountered during use.

The processing means further includes means for comparing the two frequencies of oscillation and providing an output representative of a change in the difference between these two frequencies as an indication of an incipient fire condition. As embodied herein, this comparing means includes a mixing circuit 44 to which the output of oscillators 40 and 42 are applied. Within mixer 44 the two output frequencies are beat together, and the mixer provides a signal on output line 46 which is representative of the output frequencies of oscillators 40 and 42. Preferably, the signal on line 46 is the difference or beat frequency. The output signal on line 46 is applied to additional electronic circuitry 48 with the end result being an indication of an incipient fire condition. Examples of such electronics can include a display, recording device, control device, or the like. Preferably, additional processing means, such as the type described hereinafter, are employed as an aid in negating the likelihood of a false alarm.

Particulate monitors formed by the combination of crystals 30 and 38, ocillators 40 and 42, mixer 44 and blower 16 are well known in the art and are disclosed in U.S. Pat. Nos. 3,561,253 and 3,715,911, the latter patent being assigned to the assignee of the present invention. In the general operation of these type devices, the sensing crystal 30 and the reference crystal 38 are caused to oscillate within housing 12 by the oscillating circuits 40 and 42, respectively. The blower 16 is operated to draw a sample of fluid, such as air, from the atmosphere adjacent to housing 12 into the inlet 14.

In the present invention, the incoming air sample containing the particulate matter flows through passageway 20 in nozzle block 18. The collector 24 collects a portion of this sample via opening 28, but the remainder of the sample continues through and out passageway 20, bypasses crystal 30 and is discharged from housing 12 via blower 16. The portion of the flow containing selected particulates which is tapped from the sample flows through passage 24 and exits from nozzle 36. The particulates impact upon crystal 30 and the fluid flows over this crystal and out of housing 12 via blower 16. A decrease occurs in the resonant frequency of crystal 30 due to the accumulation of particulate mass. This frequency change is sensed by oscillator 40 and results in a change in the output signal from mixer 44 where the sensing and reference oscillators are compared. This signal change is applied by line 46 to the electronics 48 to indicate the accumulation of particulate matter on crystal 30.

For a crystal operating in a shear mode, in which the opposite faces execute parallel displacements, the resonant frequency is inversely proportional to mass in cases of small amplitudes of oscillation and small variations in mass. Thus.

$$\Delta f = -Cf^2 \Delta m, \qquad (1)$$

where $\Delta f$ is the change in frequency caused by a mass change $\Delta m$, and C is a constant which has the nominal value of $2 \times 10^{-6}$, with $f$ expressed in Hertz and $m$ in grams.

From the foregoing description, it will be apparent that an increase in mass on the sensing crystal 30 will be indicated by an increase in the frequency of the output signal on line 46 from mixer 44, which represents the difference in oscillation between the sensing crystal 30 and the reference crystal 38.

The sensing crystal 30 and reference crystal 38 are preferably matched crystals and are formed of quartz, although other suitable piezoelectric material can obviously be used. The reference crystal 38 is sealed so as not to be exposed to the particulate matter in the air sample entering housing 12, and preferably is subject to the same thermal environment as the sensing crystal 30 so that any changes in temperature which may affect the oscillation of the crystals is compensated for by taking the difference in oscillation frequency between these two crystals in mixer 44. For further details as to the construction and function of a particulate monitor, attention is invited to the aforementioned U.S. patents, in particular U.S. Pat. No. 3,715,911, the content of which is herein specifically incorporated by reference.

During the making of the present invention, it was found necessary to make the collector selective with respect to particle size by setting an upper limit on the size of the particulates collected and applied to the sensing means. The critical upper limit was found to be approximately 5 microns with a preferred upper limit of 2 microns. This criticality was based on the fact that precombustion particulate emissions were found to be generally less than 5 microns with most being submicron in size, that is, less than 1 micron. In contrast, dust, fly ash and other particulates not related to an incipient fire condition generally have a size greater than the 5 micron upper limit. By such selectivity, the detector can more readily sense an increase in the concentration of particulates beyond the normal distribution, and thus the detection of an incipient fire condition is assured. The likelihood of false alarms from such as cooking, dust, housekeeping and the like, is kept small because the sensing crystal 30 is not exposed to the large-sized particulates associated with such conditions. With the upper limit set to the preferred size of 2 microns, the detector is even less responsive to particulates not generated by an incipient fire condition, although it is still able to detect most of the particulates which are generated.

Another reason for the critical upper limit has to do with operation under other than normal gravity conditions. Under normal conditions, particulates much larger than 10 microns in diameter will eventually settle to the ground in still air. Under a zero gravity condition, as might be encountered in space, these larger particulates remain in suspension. By having the detector favor the selection of small particles and reject larger ones, the present invention readily excludes the great number of large particulates found under zero gravity conditions, and thus can operate under any gravity condition.

The selection of a 5-micron upper limit also permits the utilization of Brownian motion in the operation of the invention. The phenomenon of Brownian motion keeps smaller particulates in suspension, essentially indefinitely, and can be relied upon for the diffusion of the precombustion particulates into the detecting zone of the detector 10, that is, close enough to the detector so that the particulates are drawn into the detector housing 12 by the action of the blower 16. Thus, there is no need to have the detector placed directly next to the combustible material in order to detect an incipient fire condition.

Therefore, in accordance with the invention, the collector is sized to collect at its opening, particulates having a size less than 5 microns and reject substantially all particulates having a size above 5 microns. As embodied herein and with reference again to FIGS. 2–4, the collector tube 24 is placed in passageway 20 at an angle to the planned flow of the sample through the passageway. Preferably, as shown, the detector tube is positioned to tilt forward in an upstream direction so that the front surface 26 of the tube forms an acute angle with respect to the longitudinal axis of tube 22.

As embodied herein, the size of tube 24 is determined by the equation:

$$r = \frac{V D_p^2 P_p}{18 \mu}, \qquad (2)$$

where $r$ is the radius of the tube, $V$ is the velocity of the fluid sample $D_p$ is the upper limit of the size of the particulate being collected in the tube, $P_p$ is the density of the particulate, and $\mu$ is the viscosity of the fluid sample. As an example, where $D_p$ is selected as the preferred upper limit of two microns (0.0002 cm.) and assuming the following values of:

$V = 1900$ cm per second,
$P_p = 1.4$ g/cm$^3$, and
$\mu = 0.00018$ poise, the radius $r = 0.0328$ cm.

With reference again to FIG. 4 and assuming that a tube 24 having an outside diameter of 0.0657 cm, as calculated above, has been inserted in the flow path of the primary sample in passageway 20, the flow of the sample fluid about tube 24 and the capture of particulates in opening 28 will now be described. As shown by the flow lines 50 in FIG. 4, the flow is diverted by the closed curved surface 26 around the collector tube 24 much in the manner shown. The large particles, for example, those greater than 5 microns, and also a portion of those between 2 and 5 microns are caused by a centrifugal effect to be diverted outwardly away from the surface of the collector tube 24, and they continue downstream without being captured at opening 28.

The particles of 2 microns and less, however, become submerged in the boundary layer which is created on the surface of the collector tube 24. As these particulates move around the surface of the tube and reach opening 28, they will enter opening 28, although their actual trajectories will differ depending on size. For example, the sub-micron particles, by virtue of having a lower momentum, will essentially fall into the opening; while the 1-micron and 2-micron sizes will upon reaching the edge of the opening actually follow a curved path towards its interior. Because this collector is not a perfect device, there will be some capturing of particulates in the range from 2 microns up to about 5 microns, although the number captured trails off rapidly towards the upper limit. As explained earlier, most of the particles greater than 2 microns are diverted outwardly away from the collector tube 24, and any greater than the 2micron upper limit which happen to become immersed in the boundary layer, will for the most part, pass by opening 28 without being captured.

Capturing of the particulates is aided by a slight reduction in pressure created at opening 28 by the flow of fluid around the tube. This, in effect creates a small suction in the opening 28 to draw in the particulates and fluid. The portion of the fluid sample and critical-sized particulates now pass through passageway 34 and out through nozzle 36. The captured particulates are, as explained earlier, caused to impact upon crystal 30 where they are detected. The fluid flows over and around this crystal and exits from housing 12 via blower 16.

It should now be apparent from viewing the size of the collector tube 24 and its positioning in passageway 20 that all particles smaller than the 2-micron cut-off cannot be captured. As an example, those particles which are in the two outside streamlines 50 would probably not become trapped in the boundary layer but would flow on past tube 24. What is important, however, is that those particulates which are captured be representative of the total concentration of such particulates in the sample flowing in passageway 20. As embodied herein, the particular configuration of opening 28 and the positioning of collector tube 24 in passageway 20 have been found to capture a large fixed percentage of the desired particulates from the sample, with the total captured representative of the total number and distribution of such particulates in the sample. Although the exact reason for the success of this arrangement is not understood, it seems that by tilting the collector tube forward and having a diagonally-cut opening in the tube, the flow characteristics around the tube and opening cause a substantial percentage and representative distribution of the particulates in the sample below the cut-off size to be directed down passageway 34.

Another important consideration in selecting a collector configuration is that the particulates which are captured remain a fixed percentage of the concentration of such particulates in the sample, even though the number in the sample varies. In such case, the collector in essence, follows any increase in critical-sized particulates which occur in the sample. For example, if such prticulates increase by ten percent in the sample, then the number which are captured also increase by 10 percent. This is most important in detecting an incipient fire condition because any increase in the particulates generated by such condition must be detected at crystal 30. Collector 24 has been found to have also this attribute of following such changes in concentration in the sample.

In equation (2) set forth above, the density of the particulates was stated as being equal to 1.4 g/cm$^3$. Such density is approximate, but it is representative of the organic material which constitute the sub-micron particulates generated during an incipient free condition. In contrast, inorganic particulates would have a density of approximately 2.3 g/cm$^3$. For a specific particle size, e.g. 1 micron, an inorganic particulate, therefore, has more momentum than an organic particulate. If any such inorganic particulates are present in the sample in passageway 20, their momentum makes them less likely to capture by collector 24 and their influence on the detector will be minimal.

FIG. 5 shows an alternative embodiment of a collector which operates on the same principles as collector 24 and can be used in the present invention. Collector 24a is here embodied as a tube positioned in passageway 20, at approximately a right angle to the longitudinal axis of this passageway. Opening 28a is here shown as a notch formed by removal of a portion of the back half of collector tube 24 such that this opening against faces downstream. During operation, collector 24a has also been found to collect a sample which is representative of the critical-sized particulates flowing through passageway 20, although the percentage collected is not as great as the capture percentage of the preferred collector 24. However, collector 24a has been found to maintain a constant statistical sample and any increase in the concentration of critical-sized particulates in passageway 20 is followed by the same percentage increase in collector 24a.

As described previously, the output of mixer 44 is a beat frequency proportional to accumulated mass on crystal 30. Even absent an incipient fire condition, there are a considerable number of particulates in the atmosphere below the preselected level which are captured by the collector 24 and impacted against crystal 30. Thus, under normal conditions it is to be expected that the beat frequency appearing on line 46 will increase at a substantially steady rate in response to the substantially steady increase of mass on crystal 30.

In accordance with the invention, the aforesaid processing means includes means for detecting a rate of change in the output of said sensing means above a predetermined rate in response to an increase in the rate of mass of particulates sensed by said sensing means. As embodied herein, the detecting means is responsive to the rate of change of the beat frequency or frequency difference appearing on line 46, and detects when such rate of change exceeds a predetermined rate of change.

Figure 6:
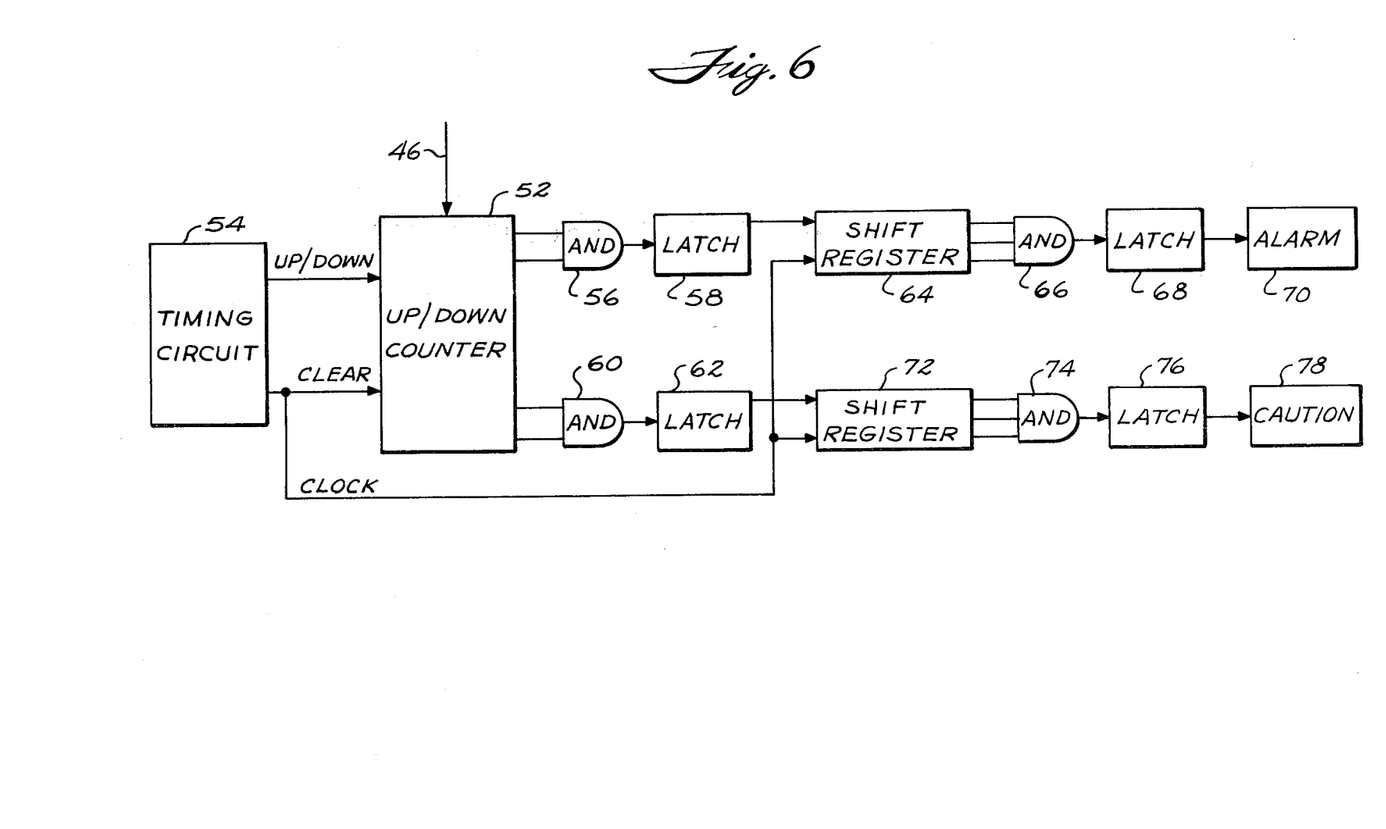
FIG. 6 is a block diagram of a preferred embodiment of the electronics to which the output of the mixer in FIG. 1 is applied.

With specific reference to the block diagram of FIG. 6, this detecting means includes an up-down counter 52 which counts the cycles of the beat frequency applied to its clock input by line 46. If desired, this AC input signal can be suitable shaped, e.g. squared, prior to application to the counter. Preferably, counter 52 counts down for 1 second and then counts up for 1 second. Because the frequency is higher during an up count than during a down count, a positive count is present at the end of each down-up count cycle. This positive count is accumulated during a fixed timing period, e.g. 2 seconds, and thus is indicative of a rate of increase in the frequency of sensing crystal 30. A timing circuit 54 controls the direction of counter 52 in a well-known manner and also applies a Clear pulse to this counter at the end of each down-up cycle.

As embodied herein, a threshold comparator 56 is connected to preselected output stages of counter 52, and a latch circuit 58 is connected to the output of comparator 56. Preferably, comparator 56 is an AND gate which is here shown as having two inputs, each of which is connected to a counter output. The output stages of counter 52 which are chosen represent a threshold count which if attained is indicative of a frequency change rate encountered during an incipient fire condition. AND gate 56 is enabled, and latch 58 is actuated when this count is attained or exceeded. An example of a threshold count is 10 Hertz.

Preferably, there is a second threshold comparator, shown here as AND gate 60, which is connected to be enabled by a count below that which enables AND gate 56. AND gate 60 is here also connected to two outputs of counter 52 of lesser significance than those connected to AND gate 56. Its output is connected to the input of a second latch circuit 62. An example of this lower threshold count is 5 Hertz.

Both gates 56 and 60 are designed to detect counts in counter 52 above those normally attained by this counter in the absence of an incipient fire condition. Assuming now that a fire is about to begin at the location of detector 10, the sub-micron particulates are generated as previously described, and a representative proportion of these particulates are captured and applied to sensing crystal 30. The beat frequency out of mixer 44 increases sufficiently so that the up count attained in counter 52 will meet or exceed the count to which AND gate 60 is responsive. This AND gate becomes enabled to operate latch 62. What this signifies is that there has been a substantial increase in the concentration of selected particulates such that the rate at which such particulates impact upon sensor 30 cause an increase in the rate of change of the beat frequency substantially above the normal rate of increase and equal to or in excess of the threshold of AND gate 60. This, then, serves as a cautionary or warning signal that there has been a substantial increase in the concentration of the critical sized particulates and that a fire may be in its incipiency. Should the concentration continue to increase so rapidly that the up count of counter 52 also meets or exceeds the threshold count of AND gate 56, then that gate is enabled and latch 58 is actuated. This serves as an alarm signal to indicate that an incipient fire is present at the location being monitored by detector 10.

By requiring that the present incipient fire detector be sensitive only to particulates in the size range of those particulates which are generated during an incipient fire condition, and by requiring that the rate of increase in the concentration of particulates exceed a threshold rate before an alarm (or cautionary) signal is given, the likelihood of the detector creating a false alarm is markedly reduced.

It is conceivable that random conditions could occur where the concentration of particulates below the cutoff size undergoes a significant increase and then drops back to its original level. Because such random increase might exceed the rate of increase to which the AND gates 56 and 60 respond, either a warning or both warning and alarm signals could be triggered, resulting in a false alarm.

To virtually negate the likelihood that a false alarm can occur, and in accordance with the invention, the aforesaid processing means includes means for determining whether said predetermined rate is exceeded for a preset time duration. Means are also provided which are responsive to said determining means for indicating an incipient fire condition. As embodied herein, said determining means includes a shift register 64 connected to the output of latch 58. The Clock input of this shift register is connected to the same output of time circuit 54 which Clears counter 52. A duration comparator is connected to the output of shift register 64. Preferably, this comparator is an AND gate 66 which is enabled when all of its inputs assume a True state. The output of AND gate 66 is connected to a latch circuit 68. As an embodiment of the indicating means an alarm 70 is provided and this alarm is connected to the output of latch 68.

In operation, up-down counter 52 preferably counts down for one second and then counts up for one second under the control of timing circuit 54. At the end of the up count, counter 52 is cleared by a clear pulse from the timing circuit. If during the up count the count reaches or exceeds the count (e.g. ten) to which AND gate 56 is responsive, this gate is enabled and latch 58 is actuated, all as previously described. A logic One is applied to the input of shift register 64. At the same time the counter 52 is cleared, a Clock pulse is applied to shift register 64 to load the One into the shift register. Latch 58 is then automatically reset in a conventional manner. Assuming that on the next down-up count cycle the preset count of 10 is again exceeded, latch 58 is again set and the Clock pulse from timing circuit 54 loads another logic One into shift register 54 and advances or shifts the logic One previously loaded. Thus, as described, logic Ones will be shifted through this register as long as latch 58 is applying a One when the Clock pulse arrives. Assuming that this is a three-stage shift register, then any time the count of counter 52 exceeds the enabling count of AND gate 56 for three consecutive count cycles, shift register 64 becomes fully loaded and AND gate 66 becomes enabled. Latch 68 is actuated and triggers alarm 70.

Obviously, time periods other than 6 seconds (three count cycles) can be selected. The duration should be sufficient to essentially eliminate the likelihood of false alarms due to a random condition or other conditions not associated with an incipient fire; yet still detect in a timely fashion an incipient fire condition. Thus, if a random condition should cause the alarm rate to be exceeded and thereby a partial loading of shift register 64, there is still no alarm actuated because the particulate rate sensed by the detector will fall below the critical level before the preselected timing period ends. During the subsequent count cycle, the up count does not exceed the threshold level of AND gate 56. Latch 58 is not actuated and a logic Zero is clocked into shift register 64. Coincidence does not occur at the inputs to AND gate 66, and alarm 70 is not actuated by this random condition.

A preset duration requirement can also be associated with the warning or caution channel and the system is identical in construction and operation to that just described for the alarm channel. As embodied herein, a second shift register 72 is connected to receive inputs from latch circuit 62 and Clock pulses from timing circuit 54. The three outputs of shift register 72 are connected to AND gate 74. The output of AND gate 74 is connected to the input of latch 76 whose output in turn is connected to the input of an indicator such as the caution indicator 78. In operation, it requires that the up count of each counting cycle exceed the count threshold of AND gate 60 for three consecutive cycles before shift register 72 is loaded with three logic Ones and AND gate 74 enabled. When such occurs, latch 76 is actuated to provide a caution indication. As explained, this arrangement also requires that the emission rate of particulates during an incipient fire condition exceed the warning threshold for a predetermined time period and thus, reduces the likelihood of a random condition causing a false warning or cautionary indication.

When a plurality of detectors 10 are employed to monitor incipient fire conditions, it may be desirable to have a central monitoring point where the output of each detector can be observed. In such case the output of latch circuits 68 and 76 in each detector can be connected into a common matrix (not shown), and then this matrix scanned or otherwise read out in a conventional manner to show the location and status of each incipient fire detector. It is preferred, although not essential, that latches 68 and 76 have a manual reset to insure that personnel who are observing the detectors for alarm or warning conditions are made aware of such conditions when they occur.

It will be apparent to those skilled in the art that modifications and variations can be made in the incipient fire detector of the present invention without departing from the scope or spirit of the invention.

What is claimed is:

1. An incipient fire detector comprising:
   a. a collector for selectively collecting particulates from a fluid flowing past said collector, said collector having:
      1. an outer surface, said outer surface being closed at the portion facing the direction of planned flow of said fluid, and
      2. an opening formed in the outer surface portion facing opposite to the direction of planned flow,
      3. said collector being sized to collect into said opening particulates having a size less than five microns and reject substantially all particulates having a size above five microns;
   b. means for sensing the particulates collected by said collector;
   c. means for directing said collected particulates from said collector opening to said sensing means; and
   d. means responsive to the output of said sensing means for processing an increase in the mass of particulates sensed by said sensing means as an indication of an incipient fire condition.

2. An incipient fire detector as claimed in claim 1 wherein:
   a. said collector is a tube sized by the equation:

$$r = \frac{V D_p P_p}{18 \mu},$$

where $r$ is the radius of the tube, $V$ is the velocity of the fluid sample, $D_p$ is the upper limit of the size of the particulate being collected in said tube, $P_p$ is the density of the particulate, and $\mu$ is the viscosity of the fluid.

3. An incipient fire detector as claimed in claim 2 wherein:
   a. $D_p$ is 2 microns, and said collector is thereby sized to collect particulates having a size less than 2 microns.

4. An incipient fire detector as claimed in claim 2 wherein:
   a. said opening is formed diagonally to the longitudinal axis of said tube.

5. An incipient fire detector as claimed in claim 4 further comprising:
   a. a housing having a passageway therethrough for passing said fluid;
   b. said tube being positioned in said passageway.

6. An incipient fire detector as claimed in claim 5 wherein:
   a. $D_p$ is 2 microns, and said collector is thereby sized to collect particulates having a size less than 2 microns.

7. An incipient fire detector as claimed in claim 6 wherein said processing means includes:
   a. means for detecting a rate of change in the output of said sensing means above a predetermined rate in response to an increase in the rate the mass of particulates are sensed by said sensing means.

8. An incipient fire detector as claimed in claim 7 wherein said processing means further includes:
   a. means for determining whether said predetermined rate is exceeded for a preset time duration; and
   b. means responsive to said determining means for indicating an incipient fire condition.

9. An incipient fire detector as claimed in claim 2 wherein:
   a. said opening is a notch in said tube formed by removal of a portion of the outer surface facing opposite to the direction of planned flow.

10. An incipient fire detector as claimed in claim 1 further comprising:
    a. a housing having a passageway therethrough for passing said fluid;
    b. said collector being positioned in said passageway.

11. An incipient fire detector as claimed in claim 8 wherein:
    a. said collector is a tube which extends into said passageway at an angle to the planned flow of said fluid; and b. said opening is formed diagonally to the longitudinal axis of said tube.

12. An incipient fire detector as claimed in claim 11 wherein:
   a. said directing means includes a passageway in said tube in flow communication with said opening.

13. An incipient fire detector as claimed in claim 12 wherein:
   a. said directing means further includes a nozzle at the end of said tube passageway for accelerating said collected particles to said sensing means.

14. An incipient fire detector as claimed in claim 13 wherein:
   a. said tube is sized to collect particulates having a size less than two microns, as determined by the equation:

$$r = \frac{V D_p^2 P_p}{18 \mu},$$

where $r$ is the radius of the tube, $V$ is velocity of the fluid sample, $D_p$ is the upper limit of the size of the particulate being collected in said tube, $P_p$ is the density of the particulate, and $\mu$ is the viscosity of the fluid sample.

15. An incipient fire detector as claimed in claim 14 wherein:
   a. said sensing means includes a sensing crystal positioned adjacent to said nozzle and having:
      1. a particulate collection surface on which the accelerated particulates are impinged.

16. An incipient fire detector as claimed in claim 15 wherein said processing means comprises:
   a. a reference crystal spaced from said sensing crystal;
   b. means for oscillating said sensing crystal at its resonant frequency;
   c. means for oscillating said reference crystal at a predetermined frequency; and
   d. means for comparing the two frequencies and providing an output representative of a change in the difference between the two frequencies as an indication of an incipient fire condition.

17. An incipient fire detector as claimed in claim 16 wherein:
   a. $D_p$ is two microns, and said collector is thereby sized to collect particulates having a size less than 2 microns.

18. An incipient fire detector as claimed in claim 14 wherein said processing means further comprises:
   a. means responsive to the output of said comparing and providing means for detecting the rate of change of said frequency difference above a predetermined rate.

19. An incipient fire detector as claimed in claim 18 wherein said processing means further comprises:
   a. means responsive to said rate change detecting means for determining whether said rate change is exceeded for a preset time duration; and
   b. means responsive to said determining means for indicating an incipient fire condition.

20. An incipient fire detector as claimed in claim 11, wherein said collector is sized to collect particulates having a size less than 2 microns and reject substantially all particulates having a size above 2 microns.

21. An incipient fire detector as claimed in claim 1 wherein said processing means includes:
   a. means for detecting a rate of change in the output of said sensing means above a predetermined rate in response to an increase in the rate the mass of particulates are sensed by said sensing means.

22. An incipient fire detector as claimed in claim 21 wherein said processing means further includes:
   a. means for determining whether said predetermined rate is exceeded for a preset time duration; and
   b. means responsive to said determining means for indicating an incipient fire condition.

23. An incipient fire detector as claimed in claim 22, wherein said collector is sized to collect particulates having a size less than two microns and reject substantially all particulates having a size above 2 microns.

24. An incipient fire detector as claimed in claim 1 wherein said collector is sized to collect particulates having a size less than 2 microns and reject substantially all particulates having a size above 2 microns.

* * * * *

UNITED STATES PATENT OFFICE
CERTIFICATE OF CORRECTION

Patent No. 3,953,844　　　　　　　　　Dated April 27, 1976

Inventor(s) Laurence Gibson Barr, et al.

It is certified that error appears in the above-identified patent and that said Letters Patent are hereby corrected as shown below:

Claim 2, line 4, in the equation after the letter "D", add the exponent --2--.

Claim 11, line 1, change "8" to --10--.

Claim 18, line 1, change "14" to --16--.

Signed and Sealed this

Twentieth Day of July 1976

[SEAL]

Attest:

RUTH C. MASON
*Attesting Officer*

C. MARSHALL DANN
*Commissioner of Patents and Trademarks*